United States Patent [19]

Curran et al.

[11] Patent Number: 5,777,121
[45] Date of Patent: Jul. 7, 1998

[54] FLUOROUS REACTION SYSTEMS

[75] Inventors: Dennis P. Curran; Sabine Hadida; Masahide Hoshino; Armido Studer, all of Pittsburgh, Pa.

[73] Assignee: University of Pittsburgh, Pittsburgh, Pa.

[21] Appl. No.: 671,945

[22] Filed: Jun. 28, 1996

[51] Int. Cl.$^6$ .............................. C07F 7/00; C07C 17/00
[52] U.S. Cl. .................. 546/2; 549/206; 556/87; 556/88; 570/241
[58] Field of Search .................. 556/87, 88; 546/2; 549/206; 510/241

[56] References Cited

U.S. PATENT DOCUMENTS 5,463,082  10/1995  Horvath et al. ........................ 549/46

OTHER PUBLICATIONS

Gronowitz et al., "The Effect of Some Additives on the Still PD0–Catalyzed Cross–Coupling Reaction," J. of Organometallic Chemistry, 460, 127–129 (1993).

Boutevin et al, "Study of the Alkylation of Chlorosilanes. Part 1. Synthesis of Tetra(1H,1H,2H,2H–polyfluoroalkyl)silanes," J. of Fluorine Chemistry, 60, 211–223 (1993).

Gladysz, "Are Teflon 'Ponytails' the Coming Fashion for Catalysts?," Science, 266, 55–56 (1994).

Horvath et al, "acile Catalyst Separation Without Water: Flurous Biphase Hydroformulation of Olefins," Science, 266, 72–75 (1994).

Zhu, "A Novel Reaction Medium: Pefrluorocarbon Fluids," Synthesis, 953–954 (1993).

Houk et al, "Stereoselective Nitrile Oxide Cycloadditions to Chiral Allyl Ethers and Alcohols. The 'Inside Alkozy Effect," J. American Chem. Soc. 106, 3880–3882 91984).

Berendensen et al., (Heptadecafluorodecyl)dimethylsily Bonded Phase for Reversed–Ohase Liquid Chromotography, Anal. Chem., 52, 1990–1993 (1980).

Stork et al., "A Catalytic Tin System for Trapping of Radicals from Cyclization Reactions. Regio–and Stereocontrolled Formation of Two Adjacent Chiral Centers," J. Ame. Chem. Soc., 108, 303–304 (1986).

Stille, The Palladium–Catalyzed Cross–Coupling Reactions of Organotin Reagents with Organic Electrophiles, Agnew. Chem. Int. Ed. Engl., 25, 508–524 (1986).

Billiet et al. "Retention and Selectivity Characteristics of Non–Polar Perfluorinated Stationary Phase for Liquid Chromotography," J. of Chromotography, 218, 443–454 (1981).

Mitchell, Paladium–Catalysed Reactions of Organotin Compounds, Synthesis, 803–815 (1992).

Deshpande, "Formation of Carbon–Carbon Bond on Solid Support: Application of the Stille Reaction," Tetrahedron Letters, 31, 5613–5614 (1994).

Wipf et al., A Solid Phase of the Biginelli Dihydropyrimidine Synthesis Suitable for Combinatorial Chemistry, Tetrahedron Letters, 43, 7819–7822 (1995).

Ugi, From Isocyanides via Four–Component Condensations to Antibiotic Syntheses, Agnew. Chem. Int. Ed. Engl., 21, 810–819, (1982).

Sisido et al. "Formation of Organotin–Nitrogen Bonds III. N–Trialkyltin–5–Substituted Tetrazoles," J. Organometallic Chem., 33, 337–346 (1971).

Hudlicky, Chemistry of Organic Fluorine Compounds, PTR Prentice Hall, New York, ix–xiv, 1, 542–545 (1992).

Davies, Comprehensive Organometallic Chemistry A Review of the Litereature 1982–1994, Pergamon, v. 217–218, 224–231, 243–245, 254, 270 (1995).

Pereyre et al, Tin in Organic Synthesis, Butterworths, London, Forward, Preface and Table of Contents (1987).

Padwa, 1,3–Dipolar Cycloaddition Chemistry, vol. 1, John Wiley & Sons, New York, v, vi, xi, 291–292 (1984).

Greene et al, Protective Groups in Organic Synthesis, John Wiley & Sons, New York, v, ix–xi, 10–15, 176–177, 224–5, 312–315 (1991).

Boutevin et al., "Study of the Alkylation of Chlorosilanes," J. of Fluorine Chemistry, 68, 71–77 (1994).

*Primary Examiner*—Porfirio Nazario-Gonzalez
*Attorney, Agent, or Firm*—Bartony Hare & Edson

[57] ABSTRACT

The present invention provides a method for carrying out a chemical reaction comprising the steps of forming an organic/fluorous solubilizing liquid phase comprising a solvent system. The solvent system is selected or adapted to substantially solubilize a fluorous reaction component or components (that is, a fluorous reagent, a fluorous catalyst and/or a fluorous reactant). The "fluorous reaction component" is functionalized to comprise at least one fluorous moiety having the formula $-(R)_d(Rf)_e$. $(Rf)_e$ is at least one fluorous group and e is a whole number. $(R)_d$ is an organic (for example, hydrocarbon) spacer group, which may be present or absent, and d is an integer equal to at least zero. The solvent system is also adapted to substantially solubilize an organic reaction component or components. After the reaction occurs in the organic/fluorous solubilizing liquid phase, a phase separation into at least a fluorous phase and an organic phase is effected. The present invention also provides a chemical compound of the formula XM|(R)(Rf)|$_3$, wherein M is Ge or Sn and X is an atom or group selected to react with an organic reaction component or components.

18 Claims, 9 Drawing Sheets

| Tin reagent<br>Substrate | ⌬—Sn(CH$_2$CH$_2$C$_6$F$_{13}$)$_3$<br>1a | MeO—⌬—Sn(CH$_2$CH$_2$C$_6$F$_{13}$)$_3$<br>1b | ⌬O—Sn(CH$_2$CH$_2$C$_6$F$_{13}$)$_3$<br>1c |
|---|---|---|---|
| C$_6$H$_5$I 5a | 90%[b] | 97% | 45%[a] |
| p-CH$_3$COC$_6$H$_4$Br 5b | 90% | 87% | 72% |
| p-NO$_2$C$_6$H$_4$OBr 5c | 94%[b] | 98% | 93% |
| p-NO$_2$C$_6$H$_4$OTf 5d | 82%[c] | 86% | 83% |
| PhCH$_2$Br 5e | 77% | 98% | 32% | a) volatile product b) the reaction solvent was THF c) the reaction solvent was DMF

*Figure 4C*

FLUOROUS REACTION SYSTEMS

FIELD OF THE INVENTION

The present invention relates to novel compositions and methods of carrying out chemical reactions.

BACKGROUND OF THE INVENTION

Organic compounds are purified on a daily basis in uncounted numbers of research and commercial laboratories and plants around the world. Purification costs account for a significant fraction of the expenses for organic compounds developed and sold by chemical, pharmaceutical, and other industries. Chromatographic methods of purification are immensely important, yet they are also expensive and time consuming. Simpler but sometimes less effective methods are based on techniques of phase separation. Four phases are commonly used in standard laboratory separation methods: a gas phase, a solid phase, and two liquid phases—organic and aqueous. Among the phase separation techniques, liquid-liquid extractions play a time-honored role in the purification of organic compounds. These extractions are almost always conducted with an organic solvent and water. Most frequently, they are used to separate (that is, purify) organic compounds from inorganic compounds. A less frequent but still important application of organic-water extractions is an acid-base extraction.

It is not widely recognized by synthetic organic chemists that there is a "third liquid phase", the fluorocarbon (or "fluorous") phase, whose members are not miscible in either water or many organic solvents. See, for example, Hudlicky, M. "Chemistry of Organic Fluorine Compounds", Ellis Horwood: Chichester (1992). As used herein, the term "fluorous phase" refers to a liquid phase comprising one or more solvents rich in carbon fluorine bonds. The fluorous phase is substantially immiscible with an "organic phase" and forms a liquid-liquid biphasic mixture with an organic phase.

As used herein, the term "fluorous", when used in connection with an organic molecule, refers generally to an organic molecule having a domain or a portion thereof rich in carbon-fluorine bonds (for example, fluorocarbons, fluorohydrocarbons, fluorinated ethers and fluorinated amines). Such portion or domain may comprise part of a fluorous compound or the entire fluorous compound. In general, organic compounds comprising a relatively high weight percentage of fluorine preferentially partition into the fluorous phase in a fluorous/organic biphase mixture. See U.S. Pat. No. 5,463,082. As used herein, the terms "fluorocarbons" and "perfluorocarbons" include organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to carbon atom has been replaced by fluorine atoms. Saturated perfluorocarbon fluids have important applications in surface chemistry, biology, and engineering. Most organic compounds are completely or substantially insoluble in fluorocarbon fluids, and many organic solvents are immiscible therein, although this miscibility depends somewhat on the fluorous-organic pairing. Solvents like carbon tetrachloride, ether, and THF have the highest solubilities in fluorocarbon fluids, and pairings of fluorocarbon fluids with these solvents are either miscible or can be made miscible by slight warming.

There are a wide assortment of fluorocarbon fluids commercially available under trade names like "FLUTEC™" and "FLUORINERT™". These fluids are made industrially by chemical or electrochemical fluorination processes. Most of these are mixtures of fluorocarbons with similar boiling points (sometimes with small amounts of fluorinated ethers). These mixtures are roughly analogous to the "petroleum ether" solvents often used in organic chemistry. Fluorinated ethers and fluorinated amines are also commercially available.

Although rarely referred to as such, these fluorocarbon "fluids" are effectively solvents. The first application of fluorocarbon solvents in the area of traditional organic synthesis appeared in 1993 when D. W. Zhu described a series of transesterification reactions in the "FLUORINERT fluid FC-77™" (a fluorocarbon mixture containing mostly isomers of $C_8F_{18}$, bp 97° C.). Zhu, D. W., Synthesis, 953–54 (1993). As illustrated in the following example, low boiling alcohols were replaced by high boiling ones, and phase separation was used at two stages.

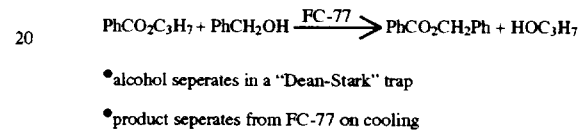

*alcohol seperates in a "Dean-Stark" trap

*product seperates from FC-77 on cooling

First, an "inverse Dean-Stark" trap was used to separate the low-boiling alcohol from the reaction mixture and thereby drive the equilibrium. Second, the product ester separated from the FC-77 on cooling. Another common fluorocarbon fluid is FC-72™, a mixture of $C_6F_{14}$ isomers with a boiling point of 56° C. FC-72 and FC-77 are commercially available from 3M.

Shortly after the work of Zhu, Horvath and Rabai described the synthesis of a "fluorous" phosphine ligand and used this to generate a rhodium catalyst for a standard hydroformylation reaction. Horvath, I. T. and Rabai, J., Science, 266, 72–75 (1994). See also U.S. Pat. No. 5,463, 082; and Gladysz, J. A., Science, 266, 55 (1994). The hydroformylation was conducted in a biphasic mixture of perfluoromethylcyclohexane (fluorous solubilizing solvent) and toluene (organic solubilizing solvent) under a $CO/H_2$ atmosphere as illustrated below.

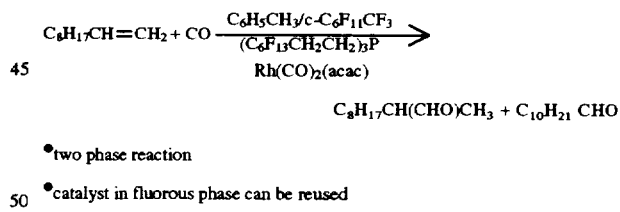

*two phase reaction

*catalyst in fluorous phase can be reused

The products were separated from the catalyst by separation of the two reaction phases, and the recovered catalyst from the fluorinated phase was successfully reused in another hydroformylation.

The distinctive physiochemical properties of a fluorous phase can be used advantageously to provide unexpected solvent effects including altered and improved product yields, reactivities and/or selectivities. Likewise, the fluorous phase can provide a valuable tool to effect separation.

It is, therefore, very desirable to develop additional fluorous reaction components, reaction systems and reaction schemes.

SUMMARY OF THE INVENTION

The present inventors have discovered that the liquid biphasic reaction systems comprising a fluorous phase and a nonfluorous phase are not operable in a number of reaction systems. Indeed, in many cases the partition coefficients for the reaction components (that is, reagents, reactants and catalysts) may be such that the phase separation between the liquid phases of biphasic systems severely inhibits or prevents reaction. It has been discovered that the processes of reaction and phase separation (that is, for recovery of product) are preferably separated.

The term "reagent," as used herein in connection with combinatorial syntheses, refers to a chemical entity that is required for a reaction but contributes either an invariant piece or no piece to the products of a combinatorial syntheses. The term "reactant," as used herein in connection with combinatorial synthesis refers generally to a type of molecule that contributes a variable piece to the products of a combinatorial synthesis. The distinction between the terms "reactant" and "reagent" in "common" (non-combinatorial) organic syntheses is vague, but those skilled in the art often refer to a reaction component as a reagent if it contributes no piece, a rather small piece, or a piece without carbon atoms therein to the target product. As used herein, the term "reagent" includes a catalyst if used in substoichiometric quantities.

As used herein, the term "substrate" refers generally to a reaction component that is a major starting material of a synthetic reaction, normally prepared in a prior step. The term "target product" refers generally to the target or desired molecule(s) of a transformation derived by reaction of the substrate with the other reaction component(s) in the medium. The terms "side product" or "byproduct" refer generally to a product derived from any component(s) of the reaction medium which is not the target product and is preferably separated therefrom. The terms "fluorous substrate," "fluorous reactant," "fluorous reagent" etc. (or, generally, "fluorous reaction component") refer generally to a reaction component comprising a portion rich in carbon-fluorine bonds. Fluorous reaction components generally partition preferentially into the fluorous phase layer (for example, a fluorocarbon or fluorohydrocarbon layer) in an organic/fluorous extraction. The term "fluorous reaction component" also includes, however, a reaction component that (1) comprises a portion rich in carbon-fluorine bonds, (2) does not preferentially partition into a fluorous phase, but (3) forms fluorous byproduct(s) comprising such a portion rich in carbon-fluorine bonds during reaction. The fluorous byproducts preferentially partition into a fluorous phase. The terms "organic substrate," "organic reactant," organic reagent etc. (or, generally, "organic reaction component") refer generally to a reaction component that partitions preferentially into the organic phase or layer in an organic/fluorous extraction.

During the course of the reaction, all of the reaction components of the reactions of the present invention, including any reagents and reactants, are preferably substantially soluble in an "organic/fluorous solubilizing liquid phase." As used herein, the term "organic/fluorous solubilizing liquid phase" refers to a liquid phase comprising a solvent system adapted or selected to substantially solubilize both an organic reaction component(s) and a fluorous reaction component(s). It is not necessary that the reaction components be completely soluble in the organic/fluorous solubilizing liquid phase at any or all times during the reaction. Each reaction component (organic or fluorous) has at least approximately a 0.1 millimolar solubility therein and, more preferably, at least approximately a 1 millimolar solubility therein. The target product and/or any byproducts need not be substantially soluble in the organic/fluorous solubilizing liquid phase. Indeed, the target product and/or any byproducts may, for example, form an immiscible liquid phase or an insoluble solid phase.

For the reactions of the present invention, such an organic/fluorous solubilizing liquid phase may comprise: (i) an organic solvent or a mixture of organic solvents (for example, carbon tetrachloride, THF and/or ether); (ii) a homogeneous mixture of an organic solvent (or solvents) with a fluorous solvent (or solvents) (for example, FC-72 mixed with carbon tetrachloride, ether or THF); or a hybrid organic/fluorous solvent (or solvents) used either alone or in combination with either or both an organic solvent (or solvents) and a fluorous solvent (or solvents). Solvent systems as described above are known in the art.

The organic/fluorous solubilizing liquid phase is a homogeneous liquid phase with respect to organic and fluorous liquid phases. As used herein, the term "homogeneous liquid phase" refers to a liquid phase in which no internal liquid-liquid physical boundaries (for example, a meniscus) are visible between an organic phase and a fluorous phase. See, for example, CRC Handbook of Chemistry and Physics, 61st Edition, C-691 (1980) (determining miscibility on the basis of either observation or absence of an interfacial meniscus). Thus, there are no internal fluorous-organic physical boundaries observed in the organic/fluorous solubilizing liquid phases of the present invention. Such organic/fluorous solubilizing liquid phases may form a liquid-liquid physical boundary with an aqueous phase in some reactions where water is present, however.

As used herein, the term "hybrid organic/fluorous solvent" refers to a solvent comprising both an organic (for example, a hydrocarbon) portion or domain and a fluorous (for example, a fluorocarbon or fluorohydrocarbon) portion or domain. In general, hybrid organic/fluorous solvents will not form a biphasic system or mixture when mixed with either organic solvents or with fluorous solvents. Some hybrid organic/fluorous may form a biphasic mixture with an organic solvent or a fluorous solvent (for example, FC-72 and $CF_3CH_2OH$ form a biphasic mixture), but such hybrid organic fluorous solvents are still useful either alone or in combination with other solvents for creating a organic/fluorous solubilizing liquid phase. Examples of hybrid organic/fluorous solvents include, but are not limited to, benzotrifluoride (BTF; $C_6H_5CF_3$), trifluoroethanol, p-chlorobenzotrifluoride ($ClC_6H_4CF_3$), and 1,4-bis (trifluoromethyl)benzene ($CF_6C_6H_4CF_3$). Examples of homogeneous mixtures of hybrid/organic solvents with organic solvents and/or fluorous solvents for use in the present invention include $BTF/CH_2Cl_2$, $H_2O/BTF/THF/$ acetone, BTF/FC-72 and BTF/FC-72/ether. Hybrid organic/fluorous solvents are somewhat analogous to hybrid organic/aqueous solvents such as alcohols (for example, $CH_3CH_2OH$) which have an organic portion and an aqueous (or water-like) portion and generally do not form a biphasic mixture when mixed with either organic solvents or water.

The present invention thus generally provides a method for carrying out a chemical reaction comprising the steps of forming an organic/fluorous solubilizing liquid phase comprising a solvent system. The solvent system is selected or adapted to substantially solubilize a fluorous reaction component or components (that is, a fluorous reagent, a fluorous catalyst and/or a fluorous reactant). The "fluorous reaction component" is functionalized to comprise at least one fluorous moiety having the formula $-(R)_d(Rf)_e$. $(Rf)_e$ is at least one fluorous group and e is a whole number. $(R)_d$ is an organic (for example, hydrocarbon) spacer group, which may be present or absent, and d is an integer equal to at least zero. The solvent system is also adapted to substantially solubilize an organic reaction component or components.

After the reaction occurs in the organic/fluorous solubilizing liquid phase, a co-solvent or co-solvents is preferably added to the organic/fluorous solubilizing liquid phase to effect a phase separation into at least a fluorous phase and an organic phase. A solid phase, a gas phase and or an aqueous phase may also be present. In some cases, it may be preferable to remove by evaporation part or all of the organic/fluorous solubilizing liquid phase before addition of the co-solvent or co-solvents. The fluorous reaction component(s) comprises a sufficient number of fluorous moieties to render any excess fluorous reaction components and fluorous byproducts derived from the fluorous reaction components preferentially partitionable into the fluorous phase after a single or a series of extractions. The organic product is preferentially partitionable into the organic liquid phase after a single or a series of extractions.

The organic spacer group $(R)_d$ may contain H and C, or may contain groups containing O, N, S, P, As and Si in addition to H and C in the backbone and/or as substituents. In general, $(R)_d$ is rich in hydrogen atoms in comparison to $(Rf)_e$. Preferably, d is an integer equal to at least zero or any whole number. More preferably, d is a whole number less than 4. Most preferably d is 0, 1, 2 or 3. In many cases, an organic spacer group is preferable or required because of the strongly electron withdrawing nature of fluorous groups. Addition of a hydrocarbon group (for example, a $—CH_2CH_2—$ group) a spacer group between the fluorous group and a reaction component generally reduces the electron withdrawing effect of the fluorous group on the reaction component. In some cases, the electron withdrawing nature of the fluorous group may have no effect or a beneficial effect upon the reaction component. In such cases, the organic spacer group may be omitted (that is, x=0).

The fluorous reaction components often may contain a plurality of fluorous moieties (for example, $Q-[(R)_d(Rf)_e]_z$, wherein Q represents a standard reaction component and $Z>1$) having a significant proportion of fluorine atoms as compared to the molecular weight of the entire reaction component. The fluorous moieties may be attached to the same atom on the fluorous reaction component(s) or to different atoms thereon. Sufficient fluorous moieties are preferably used such that any fluorous reaction components and/or any fluorous byproducts remaining after reaction are separable from the organic target product via organic-fluorous liquid-liquid extraction. However, the chemical activity of underlying reaction component Q is preferably changed little or not at all by addition thereto of fluorous portion $(Rf)_e$.

In cases in which the fluorous reaction component(s) are not completely reacted, preferably, at least approximately 20 wt % to approximately 90 wt %, and, more preferably, about 50 wt % to 90 wt % of the total weight of a fluorous reaction component comprises fluorine. In all such cases, sufficient fluorine content and appropriate structure should be present to render the fluorous reaction component preferentially partitionable in the fluorous phase after phase separation to enable separation thereof from the organic target product.

In cases in which a fluorous reaction component is used in such quantities that it is completely reacted, only the resulting fluorous byproduct(s) must be separated from the organic target product. In such cases, preferably, at least approximately 20 wt % to approximately 90 wt %, and, more preferably, about 50 wt % to 90 wt % of the total weight of a fluorous byproduct(s) comprise fluorine. As clear to one of ordinary skill in the art, if the organic portion of the fluorous reaction component was relatively large in comparison to any organic portion of the corresponding fluorous byproduct (s), the fluorine wt % of the fluorous reaction component can be less than 20 wt %. As also clear to one of ordinary skill in the art, the preferential partitioning of the fluorous reaction component into the fluorous phase in a fluorous/organic extraction is not important is these cases.

Typically, known standard (non-fluorous) reactions can be carried out under the present invention with one or more fluorous functionalized reaction components within the range of reaction conditions used in the corresponding standard reactions. The present invention is equally, however, applicable to newly developed organic reactions.

The fluorous reaction components can be prepared by fluorination or fluoro-functionalization of a starting reaction component, by modification of another fluorous reaction component, or by total synthesis. For example, fluorous tin reaction components can be made conveniently in one or more steps. An illustrative method of synthesis of fluorous tin reaction components is the combination of known nucleophiles, for example Grignard reagents such as $RfCH_2CH_2MgBr$, with known tin electrophiles, for example $Cl_3SnX$. This combination leads either directly or through the agency of one or more additional transformations wherein one group X is replaced by another to preparation of a large new class of fluorous tin reaction components $[RfCH_2CH_2]_3SnX$. The interchange of groups X in organotin chemistry is well known to those skilled in the art and can be accomplished by a large class of reactions wherein a nucleophilic precursor of the product X group replaces a leaving group X (for example, a halogen or triflate) in the tin precursor (for example, stannylation of an alcohol), by reactions wherein a tin nucleophile (X=metal) adds to or displaces an electrophile precursor of the X group (for example, a substitution reaction of a stannyl metal with an allyl halide), or by reactions in which the tin SnX bond adds to a multiple bond (for example, hydrostannation of an alkene or a carbonyl group). Similarly, the use of other standard classes of nucleophiles and tin electrophiles allows entry into related groups of reagents with other fluorous substituents on tin. Analogous transformations can generally be applied to the synthesis of related silicon and germanium reaction components.

Transformations under the method of the present invention generally parallel the transformations of known "non-fluorous" reaction components with the advantages that the fluorous reaction components and any fluorous byproducts derived from the fluorous reaction components can be removed from the organic products by liquid-liquid extraction. The recovered fluorous reaction components can often either be reused directly or recycled by standard reactions to reusable forms. These are significant advantages compared to the standard reaction components.

The method of the present invention also offers significant advantages over the current fluorous multiphase reactions. See U.S. Pat. No. 5,463,082. While there are benefits to conducting some types of catalytic and other organic reactions in multiphase systems, the vast majority of organic reactions are preferentially conducted in liquid phases in which the key reaction components have substantial solubility. Separation into immiscible fluorous and organic liquid phases is not expected to be beneficial for many important reactions classes and may often be detrimental. In the method of the present invention, fluorous reaction components and organic reaction components react under conditions in which both are substantially soluble in the same organic/fluorous solubilizing liquid phase.

For example, organic reactions of tin, germanium, and silicon reagents $R_3MX$ (where M=Si, Ge, Sn and X=an atom or a group participating in a reaction with an organic compound) are routinely used by those skilled in the art to accomplish many different organic transformations. Most reactions of these reaction components are preferentially conducted in a homogeneous liquid phase. Reactions of the fluorous analogs of these reaction components, $|(Rf)_e(R)_d|_3MX$ are likewise preferentially conducted in a homogeneous liquid phase. For example, the reagents $|C_6F_{13}CH_2CH_2|_3SiX$ where X=H and Cl are known compounds that can be used by the methods described herein to conduct reactions such as hydrosilylation and reduction (X=H) or silylation (X=Cl) that are analogous to the reactions of standard (non-fluorous) reagents $R_3SiX$ where X=H or Cl and R=alkyl or cycloalkyl. Likewise, fluorous allyl- and vinyltin and allyl- and vinylsilane reaction components can be used to for typical ionic allylations and vinylations, and fluorous allyl- and vinyltin reaction components can be used for typical radical allylations and vinylations as well. These are but a few examples selected from the rich, well known chemistry of tin, germanium and silicon.

The present invention also provides a chemical compound of the formula $$XM|(R)(Rf)|_3,$$

wherein M is Ge or Sn, X is H, F, Cl, Br, I, $N_3$, $OR^1$, OH, OOH, $OOR^1$ $SR^1$, $SeR^1$, CN, NC, $NR^1R^2$, a cyclic group (for example, an aryl group), a substituted cyclic group (for example, a substituted aryl group), a heterocyclic group (for example, a heteroaryl group), a substituted heterocyclic group (for example, a substituted heteroaryl group). Such cyclic groups are preferably of 5 to 25 carbon atoms.

X may also be a linear or branched alkyl group of 3 to 15 carbons. Further, X may be a substituted linear or branched alkyl group, an alkenyl group, a substituted alkenyl group, an alkynyl group, a substituted alkynyl, an acyl group, or a substituted acyl group. These groups preferably are of 1 to 20 carbon atoms.

X may also be M' ((R') (Rf))$_3$, OM' ((R') (Rf))$_3$ or OOM' ((R')Rf))$_3$, wherein M' is Si, Ge, or Sn, $R^1$ and $R^2$ are each independently, the same or different, H, a linear or branched alkyl group, a substituted linear or branched alkyl group, a cyclic alkyl group, a substituted cyclic alkyl group, an alkylsulfonyloxy group, a perfluoroalkylsulfonyloxy group, an acyl group, a substituted acyl group, or a perfluoroacyloxy group. R and R' are each independently, the same or different, an alkylene group of 1 to 6 carbons or a substituted alkylene group of 1 to 6 carbon atoms. Rf and Rf are each independently, the same or different, a linear perfluoroalkyl group of 3 to 20 carbons, a branched perfluoroalkyl group of 3 to 20 carbons, or a hydrofluoroalkyl group of 3 to 20 carbons, wherein the hydrofluoroalkyl group comprises up to one hydrogen atom for each two fluorine atoms thereof.

The terms "alkyl", "aryl" and other groups refer generally to both unsubstituted and substituted groups unless specified to the contrary. Alkyl can be saturated or unsaturated and branched or unbranched. Preferred substituents of substituted groups include but are not limited to groups containing C, H, Cl, F, Br, I, N, S, P, As or Si. The term "alkylene" refers to an acyclic carbon chain or a saturated acyclic carbon chain represented by the formula —$C_nH_{2n}$— (for example, —$CH_2CH_2$—), wherein hydrogen may be replaced by a monovalent substituent.

In a number of preferred embodiments, X is H, F, Cl, Br, I, $N_3$, OH, $OSn(CH_2CH_2Rf)_3$, an allyl group, a phenyl group, a 4-methoxyphenyl group, a 2-pyridyl group or a 2-furyl group, wherein M is Sn, R is a preferably a linear alkylene group of 1 to 5 carbons. Rf is a preferably a linear perfluoroalkyl chain of 6 to 12 carbons. In general, the present invention provides compounds that are fluorous analogs of standard Sn, Ge and Si compounds. Standard organometallic reaction components and reactions are reviewed in Davis, A., ed., *Comprehensive Organometallic Chemistry II*, Pergamon Press, Oxford (1995).

Fluorous compounds remaining after reactions of the present invention can be separated from organic compounds by a simple liquid-liquid extraction, thereby providing a very substantive purification that for many reactions would previously have required chromatography or some other more demanding technique. The present invention provides significant advantages in both "common" and "combinatorial" organic synthesis.

In common organic synthesis, individual steps are conducted sequentially until the final target molecule or product is made. In combinatorial organic synthesis, the target is not a single molecule but instead a "library" of tens to millions of molecules. Multiple reactions are conducted either together or in parallel to provide multiple products as individual compounds or mixtures. The techniques of combinatorial chemistry are becoming very popular in the pharmaceutical industry as tools to discover and optimize new drugs. In combinatorial synthesis, the premium of simple methods of purification is even higher than in normal synthesis; one cannot chromatograph hundreds or thousands of samples. For this reason, combinatorial synthesis is now conducted almost exclusively on the solid (polymeric) phase, where purification can be effected simply by filtration. Unfortunately, the purification attractions of the solid phase turn into synthetic detractions. Conducting liquid phase reactions can be difficult because the polymer never truly dissolves in the reaction solvent.

There are several features that favor the automation of organic synthesis with substrates in the liquid phase rather than on the solid phase. Four of these are briefly considered below.

First, there are more phases available. Counting water as three phases (neutral, acidic, basic) provides seven different phases. However, not all possible combinations can be separated (the water phases can only be separated from the other phases, not from each other). There is then much more flexibility to this approach because there are more phases and more possible separations.

Second, in the liquid phase approach with a fluorous reaction component, the substrate is not "affixed" in any phase, so purification of products by "phase switching" is now an option. Phase switching is simply modifying the substrate to so that it preferentially partitions out of one phase and into another. Classical extractions of organic amines into aqueous acid and organic acids into aqueous base are typical examples. Consider a combinatorial reaction that produces a series of carboxylic acids. When these products are on the solid phase, there is no possibility to purify them by base extraction; however, in a liquid phase approach, the acids can be purified by "switching" them from the organic phase into aqueous base. Acidification of the base phase then switches them back. Such phase switches can be envisioned between several different phases and can be accomplished at any point in a synthesis.

Third, there is no need for "attachment" and "detachment" of the substrate to the solid phase. This saves two steps per substrate, and also dismisses the requirement for a common functional group on all substrates through which attachments are made. All concerns about stabilities of polymers and linkers to reaction conditions are eliminated; the only concern is the substrates.

Fourth, many reactions will be conducted in homogenous liquid phase. This is in direct contrast to solid phase syntheses, where true homogeneity is never obtained. For many types of reactions, little or no development will be required; traditional conditions will be used directly. Heterogeneous conditions can also be used. Like solid phase reactions, reactions in the liquid phase multiplex synthesis should ideally approach quantitative yield. This is still a demanding requirement for most reactions, but one that is more readily approached at the moment in the liquid phase than in the solid phase for all but a few important reactions.

The present invention also provides a method of separating a first organic compounds from other organic compounds comprising the step of reacting the first organic compound with a fluorous reaction component to produce a fluorous compound that preferentially partitions into a fluorous phase. A fluorous/organic biphasic mixture is the created to separate the fluorous compound from the other organic compounds. After separation of the fluorous compound from the other organic compounds, the fluorous portion of the fluorous compound is cleaved to result in the first organic compound.

BRIEF DESCRIPTION OF THE DRAWINGS

FIG. 4C illustrates several examples of Stille couplings under the present invention with yields.

DETAILED DESCRIPTION OF THE INVENTION

Figure 1:
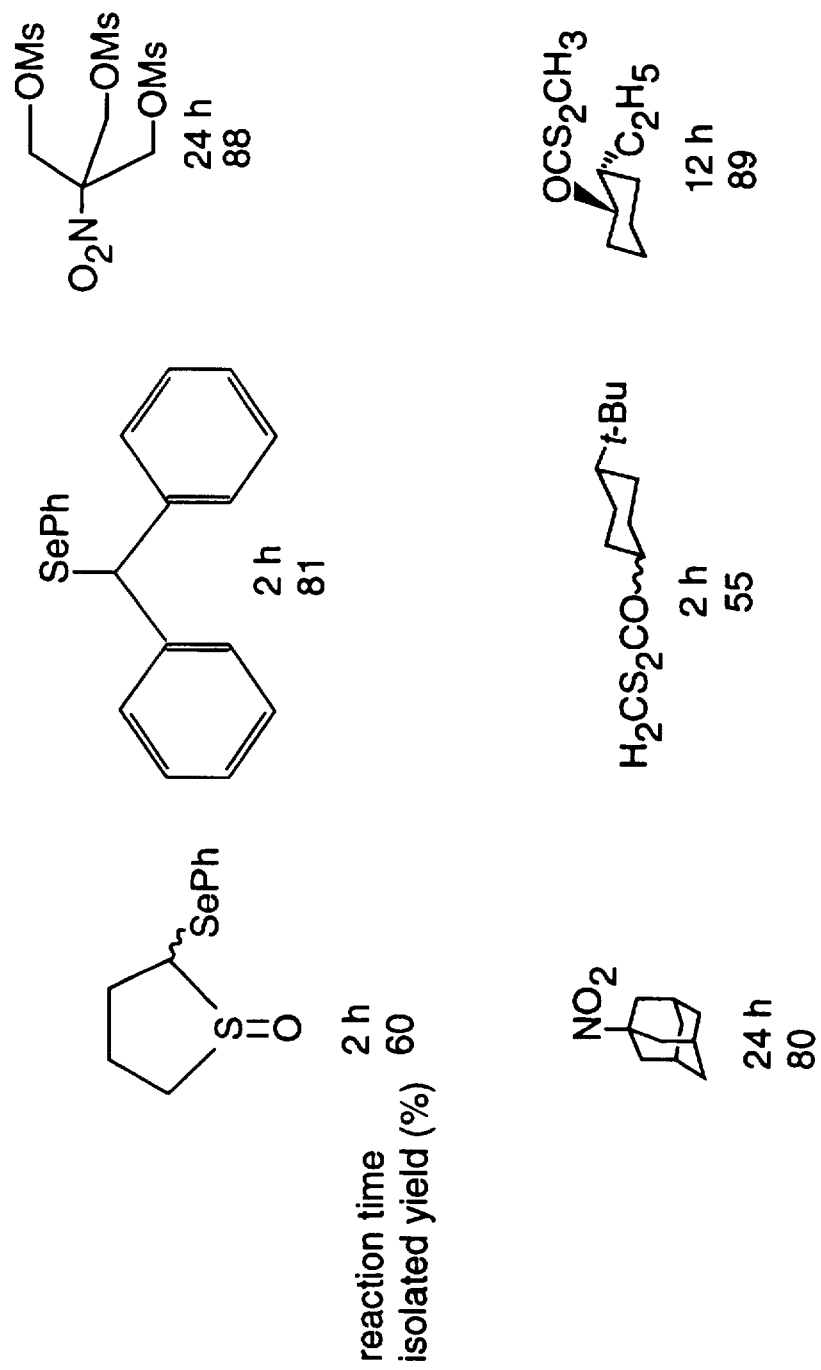
FIG. 1 illustrates organic substrates reduced with a novel fluorous reagent.

The present invention will be discussed in connection with several examples of novel fluorous synthetic schemes using reaction components (that is, reactants, reagents, and catalysts) of the general formula:

XM((R) (Rf))$_3$

In this general formula Rf is fluorous group and, preferably, a perfluorinated group having 3-20 carbons (XM[(R)$_d$(Rf)$_e$)]$_z$; wherein d=e=1 and z=3). (R) is a hydrocarbon group and, preferably a —CH$_2$CH$_2$— alkenyl group. M is selected from the group consisting of silicon, germanium and tin. X is an atom or a group that is involved in a reaction with an organic substrate. These reaction components are used in a number of different ways to synthesize and purify organic molecules, as outlined below.

Reactions of Organic Substrates with Fluorous Reagents to Provide Organic Target Products.

In this synthetic scheme, an organic substrate was reacted with a fluorous reagent of the general formula XM((R) (Rf))$_3$, which can be used in excess if desired. After reaction in an organic/fluorous solubilizing liquid phase, organic-fluorous separation/extraction upon addition of an appropriate co-solvent provides the target product in the organic phase, and the excess fluorous reagent and the products derived therefrom in the fluorous phase. The method not only facilitates purification of the target product relative to existing methods, but it also allows ready recovery of a fluorous side product in a state suitable for recycling to the original reagent for reuse. In some cases, the original reagent is recovered directly. Thus, both purification and disposal costs are reduced.

In one study, a fluorous reagent, tris (2-(perfluorohexyl) ethyl)tin hydride 3 [(C$_6$F$_{13}$CH$_2$CH$_2$)$_3$SnH] was synthesized. The approved name of fluorous tin hydride reagent 3 is tris (3,3,4,4,5,5,6,6,7,7,8,8,8-tridecafluorooctyl)tin hydride. It has been discovered that this reagent behaves very similarly to "standard" (that is, nonfluorous) tin hydride reagents in radical reductions, yet it has significant practical (and possibly also ecological) advantages over the commonly used compounds, tributyltin hydride, tris(trimethylsilyl)silicon hydride, and related reagents. In the reactions studied, a hybrid organic/fluorous solvent comprising benzotrifluoride (BTF, C$_6$H$_5$CF$_3$, trifluoromethyltoluene) or benzotrifluoride mixed with tert-butanol, was used to provide a homogeneous reaction medium or phase (the organic/fluorous solubilizing liquid phase). Homogeneous liquid phase solvents comprising mixtures of organic and fluorous solvents are known and can also be used in the reactions of the present invention. Organic solvents in which the fluorous reagent is substantially soluble (for example, hexane, THF and/or ether) can also be used. Benzotrifluoride (BTF) was selected in part because of its favorable properties and low cost.

The equation below summarizes a preferred method for preparing novel fluorous tin hydride reagent 3. Preparation of the Grignard reagent from 2-perfluorohexyl-1-iodoethane and quenching with phenyltrichlorotin provided the novel intermediate product 1a. Brominolysis of the phenyl-tin bond and reduction of the resulting novel tin bromide 2 with lithium aluminum hydride in ether provided novel fluorous tin hydride reagent 3. This product was isolated in 82% overall yield as a clear liquid after purification by vacuum distillation.

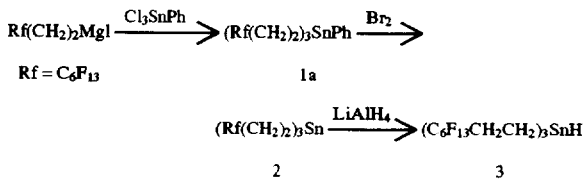

Attempts to reduce a typical organic substrate, 1-bromoadamantane, using fluorous tin hydride reagent 3 under fluorous conditions like those used by Zhu resulted in unacceptably slow reaction rates and unacceptably low yields. Similarly, attempts under fluorous biphasic conditions like those used by Horvath and Rabai or in normal organic solvents like benzene also resulted in unacceptably slow reaction rates and unacceptably low yields. It is believed that the partition coefficients for the reactants are such that the phase separation prevents a radical chain from propagating with bromoadamantane. Simple extractions provide crude estimates of partition coefficients. Fluorous tin hydride reagent 3 (1.0 g) was partitioned between PFMC (10 mL) and an organic solvent (10 mL) by shaking for 5 min in a separatory funnel. Evaporation of the organic layer provided the following weights: benzene, 22 mg; MeOH, 30 mg; $CH_2Cl_2$, 47 mg; EtOAc, 104 mg; $CHCl_3$, 141 mg.

In contrast, treatment of perfluorodecyl iodide with 1.2 equiv of fluorous tin hydride reagent 3 and 10% AIBN in refluxing PFMC provided the corresponding reduced compound 4 in 72% yield as illustrated in the equation below. The success of this fully fluorous reaction (that is, fluorous solvent, fluorous reagent, fluorous substrate and fluorous product) suggested that a homogeneous medium was important thereto.

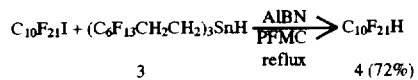

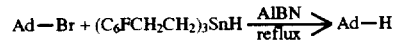

| equivalents | Solvent | yields |
|---|---|---|
| 1.2 | BTF | 90% |
| 0.1 | BTF/t-BuOH(1/1) | 92% |
| 0.01 | BTF/t-BuOH(1/1) | 95% |

Adamantyl bromide was cleanly reduced over approximately 3 hours with 1.2 equiv of fluorous tin hydride reagent 3 in refluxing BTF (stoichiometric procedure). After evaporation of the BTF and liquid-liquid extraction (PFMC-$CH_2Cl_2$) to separate the tin products, adamantane was isolated in 90% yield (as determined by GC integration). Under the stoichiometric procedure, fluorous tin hydride reagent 3 reduces a number of other functional groups besides halides, as shown in FIG. 1. In these substrates, the nitro, phenylseleno, or xanthate groups are replaced by hydrogen.

A catalytic procedure was also developed by using 10% fluorous tin hydride reagent 3 and 1.3 equiv of $NaCNBH_3$ in a 1/1 mixture of BTF and tert-butanol at reflux. This procedure is analogous to the "standard" reaction developed by Stork for nonfluorous tin hydrides. Stork, G. and Sher, P. M., *J. Am. Chem. Soc.*, 108, 303 (1986). After approximately 3 hours, the reduction of 1-bromoadamantane was complete. After evaporation, the products were isolated by partitioning between three liquid phases: water removes the inorganic salts, methylene chloride extracts the adamantane (isolated in 92% yield), and perfluoromethylcyclohexane extracts the tin products. Analyses by $^1H$ NMR and $^{19}F$ NMR (estimated detection limit 1-2%) failed to detect any fluorinated products in the residue from the methylene chloride phase, and likewise no adamantane was detected in the fluorous extract. The residue from the fluorous extract was reused five times to reduce bromoadamantane by this catalytic procedure with no decrease in yield. In separate experiments, successful reductions of 1-bromoadamantane were observed with as little as 1% of the fluorous tin hydride reagent 3. A control experiment showed that 1-bromoadamantane was not reduced by $NaCNBH_3$ alone under these conditions over approximately 24 hours.

Synthetic chemists have long lauded the ionic and radical reactivity profile of tributyltin hydride, but bemoaned its separation and toxicity problems. The results of the present studies indicate that fluorous tin hydride reagent 3 retains the laudable reactivity profile of tributyltin hydride. However, fluorous tin hydride reagent 3 can be separated from organic products by liquid-liquid extraction. The ability to use fluorous tin hydride reagent 3 in catalytic amounts and to repeatedly reuse the fluorous residue indicates that large scale applications of fluorous tin hydride reagent 3 or a suitable relative are practical because it is not necessary to synthesize or to dispose of large quantities of tin. A family of related tin reagents can provide similar practical benefits for other important organotin reactions. A review of non-fluorous (standard) tin reactions is provided in Pereyre, M.; Quintard, J. P. and Rahm, A., *Tin in Organic Synthesis*, Butterworths: London; (1986).

Figure 2A:
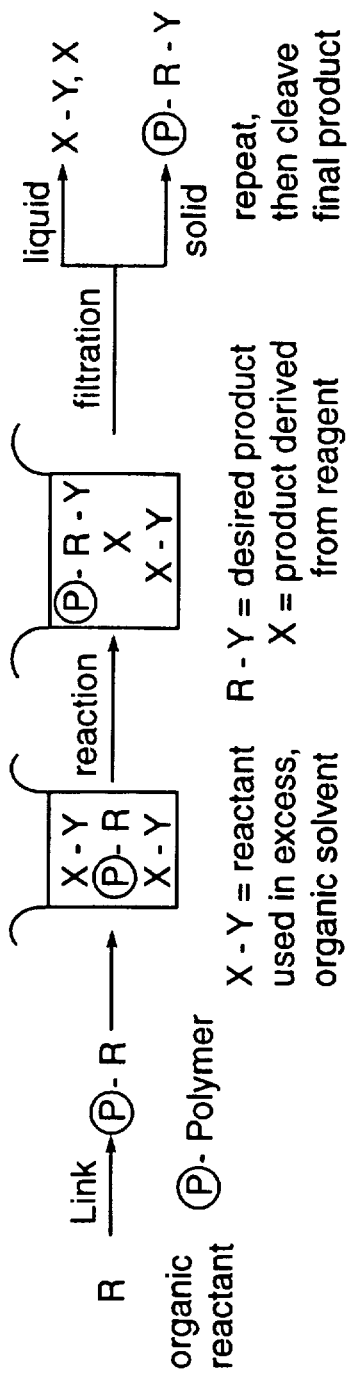
FIG. 2A illustrates a current combinatorial synthetic scheme.
Figure 2B:
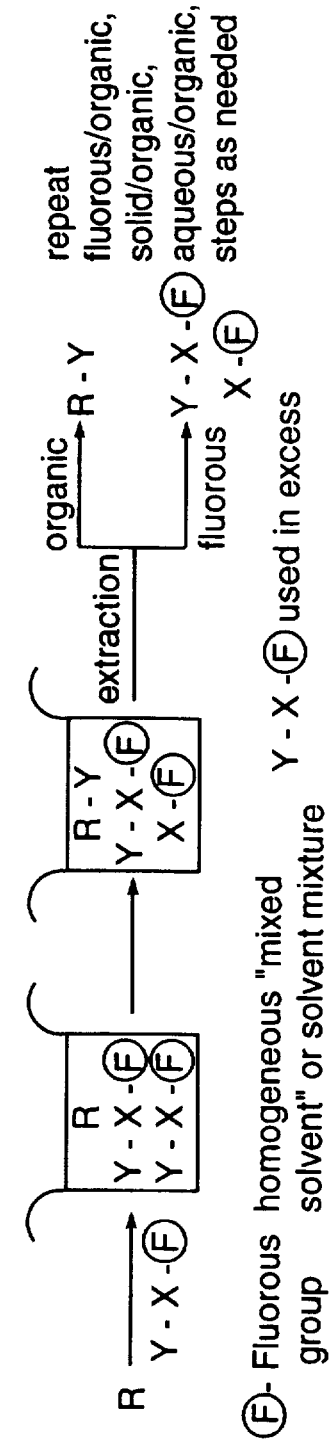
FIG. 2B illustrates an embodiment of a combinatorial synthetic scheme of the present invention.

Fluorous reagents such as fluorous tin hydride reagent 3 also have important applications in combinatorial synthesis. Most current combinatorial synthetic strategies place the substrate on a polymeric solid phase (P) (see FIG. 2A) so that it can be separated from other compounds in the reaction mixture by the phase separation technique of filtration. However, there are a number of synthetic advantages to combinatorial strategies that place the substrate in the organic liquid phase, especially for syntheses of relatively small libraries (for example, tens to hundreds of compounds). Fluorous reagents provide new options for these types of syntheses because fluorous reagents and the substrates (organic soluble) can be separated by the phase separation technique of extraction. See FIG. 2B.

Figure 3:
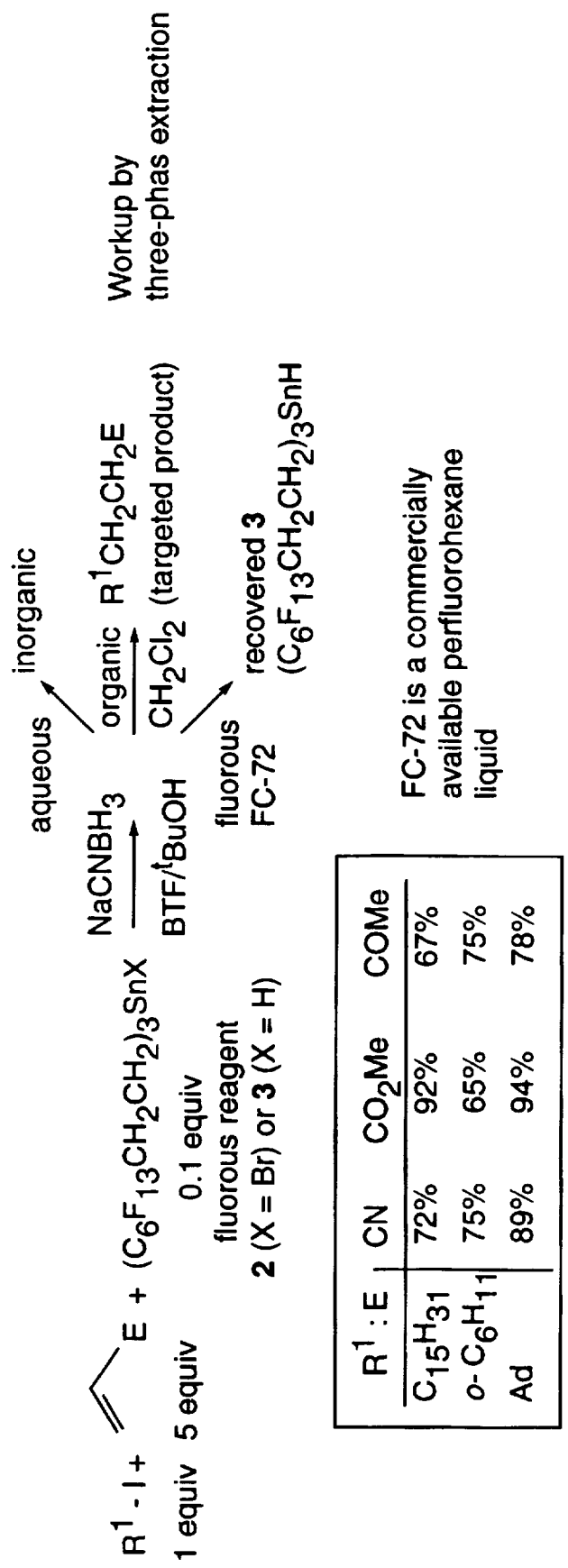
FIG. 3 illustrates the results of a combinatorial synthesis under the present invention.

To illustrate the possibilities, a "fluorous/organic" step was simulated in a homogeneous liquid phase combinatorial synthesis by conducting a series of radical additions in parallel. The results are illustrated in FIG. 3. Three halides were crossed with three alkenes, and reductions were conducted simultaneously in nine individual vials under the catalytic procedure. The nine products were "purified" by three-phase liquid-liquid extraction (conducted in the original reaction vial) and evaporation. Yields were then determined by recording NMR spectra in the presence of an internal standard. The crude products were quite pure (no significant starting materials or side products as assayed by capillary GC), and could hypothetically be used directly in the next step of a sequence. Automation of the extractions would make more parallel reactions possible.

Combinatorial synthesis with substrates in the organic liquid phase can already be conducted without chromatography if all the other reagents are volatile, water soluble, or on a solid phase. In the case of fluorous reagents, the possibilities for liquid phase combinatorial synthesis in a spatially separated mode are greatly expanded. Like filtration, the phase separation techniques of extraction and evaporation also allow ready separation of components, so excesses of reagents can be used. The pairing of organic substrates with fluorous reagents is expected to be especially important since a full range of traditional (including anhydrous) reactions can be conducted under homogenous liquid phase conditions, yet the products and reagents can still be separated by extraction. In short, the detractions to synthesis posed by phase separation can be divorced from its advantages in purification.

Reactions of Organic Substrates with Fluorous Reactants to Provide Organic Target Products.

The features of this synthetic scheme are similar to those described above, except that a fluorous reactant reacts with an organic reaction component. The method of the present invention is illustrated with a combinatorial Stille coupling in FIG. 4B. A standard Stille coupling is illustrated in FIG 4A.

Figure 4A:
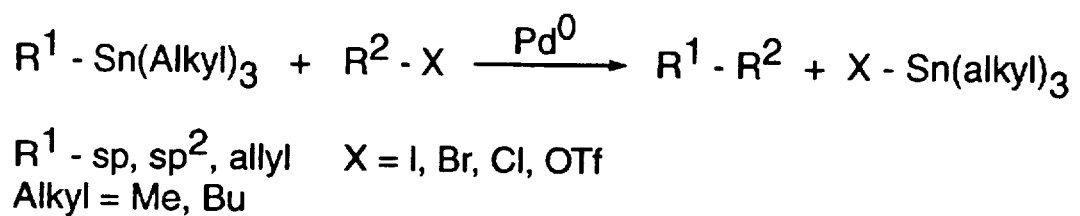
FIG. 4A illustrates a standard Stille coupling.

The standard Stille reaction as illustrated in FIG. 4A is an important member of a family of transition metal catalyzed cross coupling reactions that is regularly used in modern organic synthesis, and it has recently been extended to solid phase combinatorial synthesis. Stille, J. K., *Angew. Chem Int. Ed. Engl.*, 25, 508 (1986); Mitchell, T. N., *Synthesis*, 803 (1992); Deshpande, M. S., *Tetrahedron Lett.*, 35, 5613

(1994). The characteristic feature of the standard Stille reaction is that one of the coupling partners is a trialkylorganotin compound (see FIG. 4A). The alkyl substituents are almost always methyl or butyl groups. The Stille reaction is popular because the tin reagents are relatively air and moisture stable, can be easily synthesized and purified, and tolerate a wide variety of both protected and unprotected functional groups. After the Stille reaction, the tin becomes a liability: trimethyltin byproducts are easy to remove but toxic, while tributyltin compounds are less toxic but difficult to remove.

The present inventors have discovered that compounds of the general structure $ArSn(CH_2CH_2C_6F_{13})_3$ participate in representative Stille couplings to make biaryls and diarylmethanes, and that all the advantages of the fluorous synthetic scheme of the present invention are exhibited. The present studies teach new options for the emerging field of liquid-phase combinatorial synthesis.

Fluorous phenyl tin reactant 1a served as one of the reactants for a Stille coupling. Brominolysis of 1a as described above provided the tin bromide 2, which served as the precursor for preparing the p-methoxyphenyl-(1b), 2-furyl-(1c) and 2-pyridyl-(1d) fluorous tin reactants by standard reactions with either aryllithium or aryl Grignard reagents.

Figure 4B:
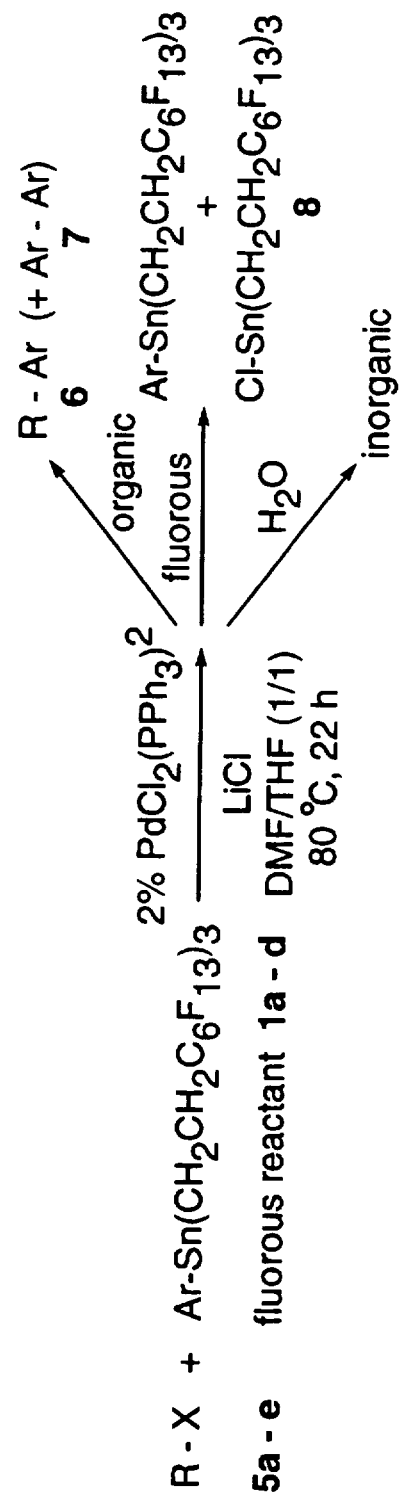
FIG. 4B illustrates a Stille coupling under the present invention.

Stille reactions were conducted under the standard set of conditions illustrated in FIG. 4B. These conditions were selected based on a number of trial experiments with fluorous aryl tin reactants 1a–d. Because Stille reactions are not generally conducted under biphasic conditions, a solvent system that substantially solubilized both the organic substrate and the fluorous tin reactant and that provided clean transformations within a reasonable time frame was used. DMF and THF were both useful, but reactions were rather slow (approximately 2 days). Solvents comprising equal parts of DMF/THF and solvents comprising equal parts of $DMF/C_6H_5CF_3$ both provided homogeneous liquid phase reactions (as determined by observation) and reasonable reaction rates (<22 hours) at 80° C. The DMF/THF mixture (1/1) was selected for the standard experiments.

A mixture of 1.2 equiv fluorous tin reactant (1a–d), 1 equiv halide or triflate (5a–e, 0.2 mmol), 2% $PdCl_2(PPh_3)_2$, and 3 equiv of LiCl in 1/1 DMF/THF (1 mL) was heated at 80° C. Reactions were conducted in individual vessels in groups of five (one tin reagent with all five partners). After approximately 22 hours, each mixture was evaporated to remove some of the solvent and then was partitioned in a three-phase extraction between water (top), dichloromethane (middle) and FC-72 (bottom). Evaporation of the FC-72 phase provided fluorous tin chloride 8 $(C_6F_{13}CH_2CH_2)_3SnCl$ (80-90%). Most of the residual 10-20% fluorous tin chloride 8 remained in the organic phase. If desired, the residual amount can be removed by washing with FC-72. Recovered fluorous tin chloride 8 was routinely recycled. Evaporation of the organic phase provided a crude organic product that was further purified by preparative TLC to provide major cross-coupled biaryl or diarylmethane 6 along with small amounts of symmetrical biaryl 7 (5–10%) derived from the tin reactant. The symmetrical biaryl is a common byproduct in standard Stille couplings.

Yields for the cross-coupled products are shown in FIG. 4C for fluorous tin reactants 1a–c. These reactants gave very clean crude products, and isolated yields of target product 6 were generally high (>80%), except for a few cases with the furyl tin reagents where the products are somewhat volatile. As in the case of the standard Stille coupling of 2-pyridyltributytin reagent, the five crude products from the pyridyl tin reagent 1d were not very clean, so these reaction mixtures were not fully purified. See Gronowitz, S. et al., "The Effect of Some Additives of the Stille $Pd^0$-Catalyzed Cross-Coupling Reaction, J. of Organometallic Chem., 460, 127 (1993). Significant amounts of cross-coupled products (estimated 25 to 50%) were produced with p-nitrophenyl triflate and bromide and with iodobenzene; however, yields of pure products were not determined.

A preparative reaction was conducted with 0.40 g of p-bromonitrobenzene (2 mmol) and 2.97 g of phenyltin reactant 1a (2.4 mmol) in 10 mL 1/1 DMF/THF at 80° C. for approximately 22 hours. Both reactants were consumed according to TLC analysis. After azeotropic evaporation with toluene at 75° C. (to remove some of the solvent), a three-phase extraction was conducted as described above. The methylene chloride phase was then washed three more times with water and FC-72 (together) to remove DMF and fluorous products. The crude organic product was purified by flash chromatography to provide 337 mg (85%) of 4-nitrobiphenyl and 17 mg (5%) of biphenyl. The crude fluorous tin chloride (99%) from the FC-72 phase was reacted with phenyl magnesium bromide to provide 2.85 g (96% overall) of the original tin reactant 1a after purification by passing through a short column of neutral alumina.

The success of the Stille reaction coupled with the prior radical and ionic reactions of the analogous tin hydride indicate that rendering other tin reactant fluorous can be a general strategy to make the vast repertoire of organotin chemistry more practical and more environmentally friendly.

Reaction of Organic Substrates with Fluorous Reagents (or Reactants) to Provide Fluorous Target Products which are Later Converted to Organic Target Products.

Under this synthetic technique, which may be used in a manner similar to a classic acid/base extraction (involving liquid-liquid extractions between organic solvents and water), an organic substrate is reacted with a fluorous reagent or a fluorous reactant to provide a fluorous target product. Fluorous-organic separation then provides the target product in the fluorous phase. The organic phase contains any unreacted substrate, any impurities in the substrate that did not react with the reagent, and any organic side products. Subsequent cleavage of the fluorous functional group then provides a purified organic target product after fluorous-organic extraction. Left in the fluorous phase are any unreacted substrate from the second reaction, any unreacted fluorous reagent from the first reaction, and all fluorous side products. This double extraction allows the target organic product to be separated from both fluorous and organic impurities. Two examples of this technique using the tin azide reactant are illustrated in FIGS. 5 and 6 and are summarized below.

Figure 5:
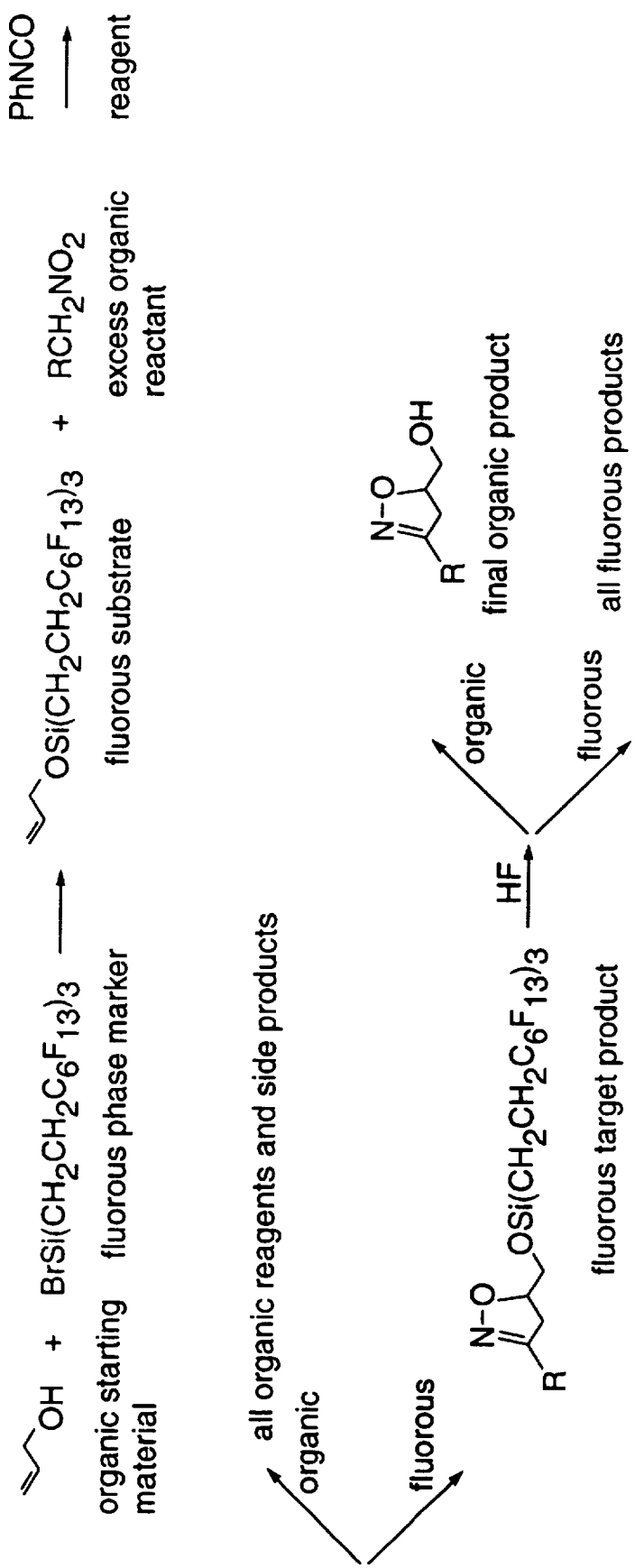
FIGS. 5 and 6 illustrate examples of the reaction of organic substrates with fluorous reagents to provide fluorous target products.
Figure 6:
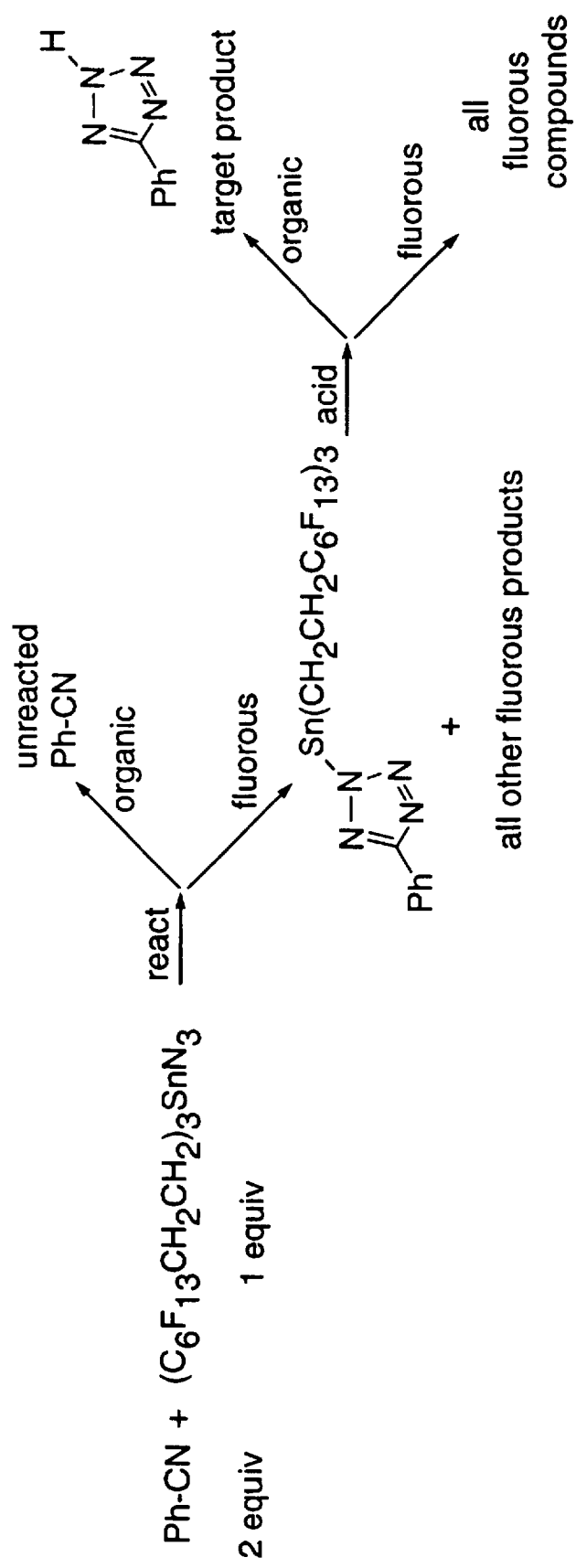

In the example illustrated in FIG. 5, an excess of nitrile was deliberately used to simulate a reaction that does not go to completion. In the example illustrated in FIG. 6, an impurity was deliberately added to simulate a prior incomplete reaction (in this case, a hypothetical synthesis of a nitrile from a halide). In both cases, the organic target product was separated from the organic "impurities" and all fluorous components.

Reactions of Fluorous Substrates with Organic Reactants to Provide Fluorous Target Products.

Figure 7:
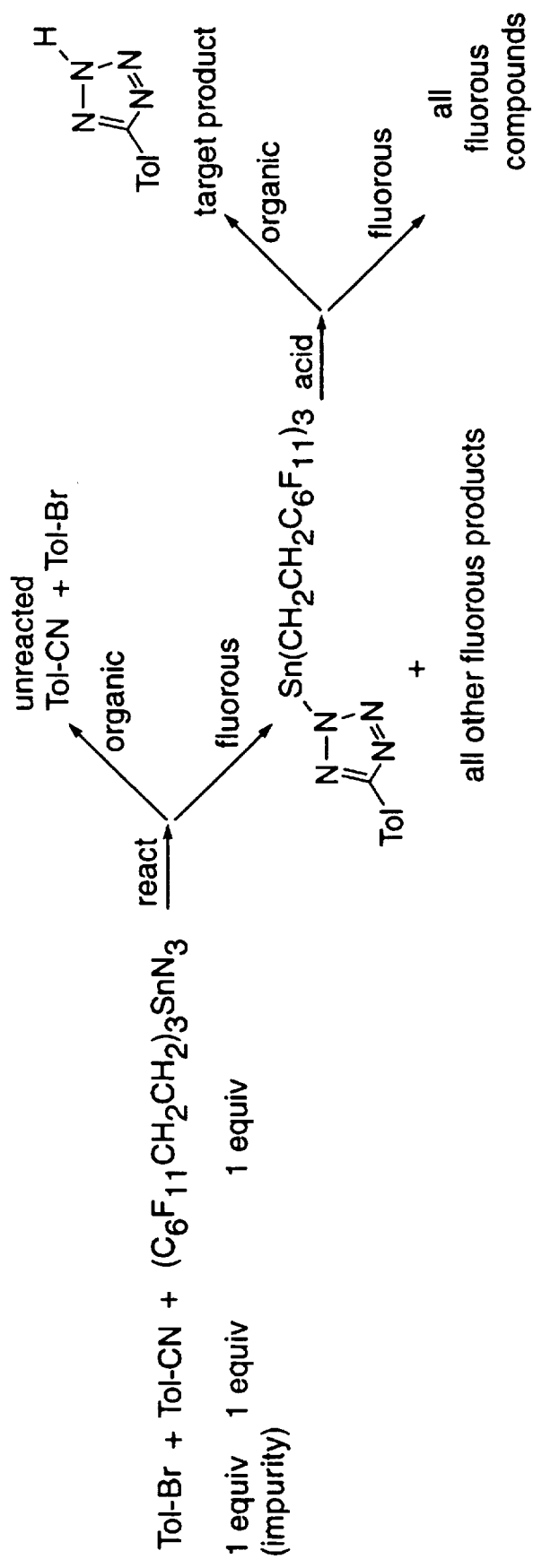
FIG. 7 illustrates an example of reaction of a fluorous substrate with an organic reactant to provide a fluorous target product.

This synthetic scheme is analogous to the now common use polymers in large molecule synthesis and combinatorial chemistry, but the method of the present invention has the advantage of allowing the routine use of standard liquid phase reagents and reaction conditions. To begin a synthesis, an organic substrate is rendered fluorous by attachment to a fluorous group (for example, a silyl or a stannyl group) that acts as a "fluorous phase marker." A reaction or sequence of reactions is then conducted in which the products are purified by, for example, phase separation techniques including liquid-liquid extraction (for organic or water soluble reagents, reactants, impurities), filtration (for polymeric or solid reagents, reactants, impurities) or evaporation (for volatile reagents, reactants, impurities). At the end of the synthesis, the target organic product is released from the fluorous marker, and then separated from all fluorous products by a liquid-liquid extraction (or filtration, if the target product is a solid). The nitrile oxide cycloaddition illustrated in FIG. 7 exemplifies this synthetic scheme for a one step reaction sequence. To demonstrate the purification possibilities, excess reagents were used. After extraction, the fluorous product was separated from all the byproducts by liquid-liquid extraction. Treatment of this fluorous product with aqueous 1N $H_2O$ acetone then liberated the ultimate organic target product. Though only one step was conducted, the potential for multi-step reaction sequences is evident.

EXPERIMENTAL EXAMPLES

1. Preparation of tris (3,3,4,4,5,5,6,6,7,7,8,8,8-Tridecafluorooctyl)phenyltin, (tris (2-Perfluoro-hexylethyl) phenyltin) (1a):

To the Grignard reagent prepared from 2-perfluorohexyl-1-iodoethane (100 g, 211 mmol) and magnesium (6.53 g, 269 mmol) in dry ether (150 mL) was added phenyltin-trichloride (15.9 g, 52.7 mmol) dissolved in dry benzene (100 mL). After refluxing for 4 h, the reaction was stirred for 16 hours at 25° C. The reaction mixture was hydrolyzed with $NH_4Cl$ solution, and the organic phase was washed with 5% $Na_2S_2O_3$ solution and deionized water, and then dried over anhydrous $MgSO_4$. The solvent was evaporated to dryness. After removal of the major byproduct bis (1,4-perfluorohexyl)butane by vacuum distillation (87°–92° C., 0.2 mm Hg), the resulting residue was purified by column chromatography on neutral alumina with hexane to give pure compound 1a (56.1 g, 86%) as a colorless oil.

$^1H$ NMR ($CDCl_3$) d 7.41 (s, 5 H), 2.31 (m, 6 H), 1.31 (t, J=8.3 Hz, $^2J$ ($^{119}Sn$—H)=53.4 Hz, 6 H); $^{119}Sn$ NMR ($CDCl_3$)–11.7 ppm; IR (thin film) 3100, 2950, 1238, 1190, 1144, 655 cm$^{-1}$; MS (m/z) 1161 (M$^+$-Ph), 891 (M$^+$—$CH_2CH_2C_6F_{13}$).

2. Preparation of Bromo tris (3,3,4,4,5,5,6,6,7,7,8,8,8-Tridecafluorooctyl) Tin, (Bromo tris (2-perfluorohexyl) ethyltin) (2):

Bromine (5.83 g, 36.5 mmol) in ether (10 mL) was added dropwise to an ice-cold solution of 1a (43.0 g, 34.8 mmol) in dry ether (80 mL). The mixture was warmed to 25° C. over 2 h with stirring. Removal of the ether, bromobenzene, and excess of bromine by evaporation under reduced pressure resulted in an orange oil. Purification by vacuum distillation (150°–152° C., 0.5 mm Hg) yielded compound 2 (42.4 g, 98%) as a colorless oil.

$^1H$ NMR ($CDCl_3$) d 2.42 (m, 6 H), 1.56 (t, J=8.3 Hz, $^2J$ ($^{119}Sn$—H)=53.4 Hz, 6 H); $^{119}Sn$ NMR (hexane) 259.2 ppm (m); IR (thin film) 3600, 1250, 1227, 1145, 534 cm$^{-1}$; MS (m/z) 1161 (M$^+$—Br), 893 (M$^+$—$CH_2CH_2C_6F_{13}$).

3. Preparation of tris (3,3,4,4,5,5,6,6,7,7,8,8,8-Tridecafluorooctyl)tin Hydride, (tris (2-Perfluorohexyl) ethyltin Hydride) (3):

An ethereal solution of $LiAlH_4$ (0.8 mL, 0.8 mmol) (1M) was added dropwise to an ice-cold solution of tris (2-perfluorohexyl)ethyltin bromide (1.0 g, 0.8 mmol) in ether (20 mL) and the reaction mixture was stirred for 3 h at 0° C. The reaction mixture was quenched by slowly adding water (5 mL), followed by 20% sodium potassium tartrate solution (20 mL). After separation of the ethereal layer, the aqueous phase was extracted with ether (3×25 mL), and the combined extracts were dried over anhydrous $MgSO_4$. Removal of the ether by distillation yielded a slightly yellow liquid which was fractionated under reduced pressure. The fraction, boiling at 145°–150° C., 3 mm Hg was collected yielding 910 mg (97%) of the hydride 3 as a colorless oil.

$^1H$ NMR ($CDCl_3$) d 5.27 (s, 1 H), 2.35 (m, 6 H), 1.16 (t, J=8.1 Hz, $^2J$ ($^{119}Sn$—H)=53.4 Hz, 6 H); $^{119}Sn$ NMR ($CDCl_3$)–84.5 ($^1J$ ($^{119}Sn$—H)=1835 Hz); IR (thin film) 1842, 1197 cm$^{-1}$ MS (m/z) 1161 (M$^+$—H), 813 (M$^+$—$CH_2CH_2C_6F_{13}$).

4. Representative Stoichiometric Experimental Procedure for Fluorous Tin Hydride Reductions:

To a stirred solution of 1-bromoadamantane (100 mg, 0.46 mmol) and tris (2-perfluorohexyl)ethyltin hydride (640 mg, 0.55 mmol) in benzotrifluoride (9.2 mL) was added a catalytic amount of AIBN. The reaction mixture was heated at reflux temperature for 3 h. The solvent was evaporated and the crude residue was partitioned between dichloromethane (20 mL) and perfluoromethylcyclohexane (10 mL). The two layers were separated and the dichloromethane phase was concentrated yielding adamantane as a pure compound (56 mg, 90%).

5. Representative Catalytic Experimental Procedure for Fluorous Tin Hydride Reductions:

A suspension of 1-bromoadamantane (347 mg, 1.60 mmol), bromo tris 2-(perfluorohexyl)ethyltin (200 mg, 0.16 mmol), sodium cyanoborohydride (138 mg, 2.1 mmol) and AIBN (in catalytic amount) in benzotrifluoride (1.6 mL) and tert-butanol (1.6 mL) was heated in a sealed tube at reflux during 3 h. The solvent was evaporated and the crude residue was partitioned between water (10 mL), dichloromethane (15 mL) and perfluoromethylcyclohexane (10 mL). The three layers were separated and the dichloromethane phase was dried over $MgSO_4$ yielding, after evaporation, adamantane as a pure compound (200 mg, 92%).

6. Representative Combinatorial Chemistry Experimental Procedure for Fluorous Tin Hydride Reductive Additions:

In a typical experiment, a suspension of alkyl iodide (0.1 mmol), olefin (0.5 mmol), bromo tris 2-(perfluorohexyl) ethyltin (12.4 mg, 0.01 mmol), sodium cyanoborohydride (9.6 mg, 0.13 mmol) and AIBN (in catalytic amount) in BTF (0.5 mL) and tert-butanol (0.5 mL) was heated at reflux in a sealed vial for 12 h.

To the cooled reaction mixture, PFMC (2 mL) and dichloromethane (1 mL) were added. After separation of the 2 phases, the dichloromethane phase was extracted another time with PFMC (1 mL) and then with water (1 mL). The organic phase was filtered through neutral alumina and evaporated to dryness. The yields of this reactions were determined by $^1H$ NMR using $CH_2Cl_2$ and hexamethyldisiloxane as internal standards (See FIG. 3).

7. Representative Experimental Procedure for Fluorous Tin Hydride Reductive Cyclizations:

A suspension of hexenyl bromide (0.32 mmol), bromo tris (2-perfluorohexyl)ethyltin (40 mg, 0.032 mmol), sodium cyanoborohydride (28 mg, 0.42 mmol) and AIBN (in catalytic amount) in BTF (3.2 mL) and tert-butanol (3.2 mL) was heated at reflux in a sealed tube. The progress of the reaction was monitored by TLC. The solvent was evaporated and the crude residue was partitioned between water (8 mL), dichloromethane (15 mL) and FC-72 (12 mL). The three layers were separated and the dichloromethane phase (middle layer) was extracted twice with FC-72 (2×10 mL), dried over MgSO$_4$ yielding, after evaporation, the cyclopentane derivative. Starting from 6-bromo-1,1-diphenylhexene and 7-bromohept-2-enenitrile, diphenylmethylcyclopentane and cyclopentaneacetonitrile were isolated in 75 and 66% yield respectively.

8. Representative Procedure for Fluorous Tin Hydride Ionic Reductions of Aldehydes:

A solution of aldehyde (0.144 mmol), zinc chloride (393 mg, 2.88 mmol), tris (2-perfluorohexyl)ethyltin hydride (104 mg, 0.09 mmol) in ether (2.9 mL) was heated at reflux in a sealed tube. The progress of the reaction was monitored by TLC. The solvent was evaporated and to the crude residue was added water (2 mL), dichloromethane (5 mL) and PFMC (4 mL). The three resulting layers were separated and the dichloromethane layer (middle layer) was extracted twice with PFMC (2×5 mL), dried over MgSO$_4$, filtered through silica and evaporated under reduced pressure to yield the pure alcohol. In that way, benzyl alcohol, p-nitrobenzyl alcohol and 3-phenyl-1-propanol were obtained from benzaldehyde, p-nitrobenzaldehyde and 3-phenylpropanaldehyde in 78, 64 and 68% yield respectively.

9. Preparation of tris (3,3,4,4,5,5,6,6,7,7,8,8,8-Tridecafluorooctyl)(4'-methoxyphenyl)tin, (tris (2-Perfluorohexylethyl)(4'-methoxyphenyl)tin) (1b):

To the Grignard reagent prepared from 4-bromoanisole (681 mg, 3.64 mmol) and magnesium (102 mg, 4.20 mmol) in dry ether (20 mL) was added a solution of 2 (3.47 g, 2.80 mmol) in dry ether (10 mL). After refluxing for 1 h, the reaction was stirred for 16 h at 25° C. The reaction mixture was quenched with NH$_4$Cl solution and diluted with ether, and the organic phase was washed with deionized water then dried over anhydrous MgSO$_4$. The solvent was evaporated to dryness. Purification by vacuum distillation (166° C., 0.25 mm Hg) and then column chromatography on neutral alumina with hexane yielded pure compound 1b (5.20 g, 74%) as a colorless oil.

$^1$H NMR (CDCl$_3$) d 7.30 (d, J=8.3 Hz, 2 H), 6.98 (d, J=8.3 Hz, 2 H), 3.82 (s, 3 H), 2.29 (m, 6 H), 1.27 (t, J=8.3 Hz, $^2$J ($^{119}$Sn—H)=54.0 Hz, 6 H); $^{119}$Sn NMR (CDCl$_3$) 123.7 ppm; IR (thin film) 1500, 1375, 1240, 1205, 1145, 1065, 745, 700 cm$^{-1}$; MS (m/z) 1267 (M$^+$), 1161 (M$^+$—C$_6$H$_4$OMe), 921 (M$^+$—CH$_2$CH$_2$C$_6$F$_{13}$).

10. Preparation of tris (3,3,4,4,5,5,6,6,7,7,8,8,8-Tridecafluorooctyl)(2'-furyl)tin, (tris (2-Perfluorohexylethyl) (2'-furyl)tin) (1c):

To a solution of furan (667 mg, 9.80 mmol) in dry THF (25 mL) at 0° C. was added a 1.5M solution of LDA in cyclohexane (6.53 mL, 9.80 mmol). After stirring 1 h at 0° C., the resulting mixture was treated with a solution of 2 (8.67 g, 7.00 mmol) in dry THF (15 mL). The reaction mixture was warmed to 25° C. over 1 h and then stirred for 16 h at 25° C. The reaction mixture was quenched with NH$_4$Cl solution and diluted with ether. After separation, the organic phase was washed with deionized water and then dried over anhydrous MgSO$_4$. The solvent was evaporated to dryness. Column chromatography on neutral alumina with hexane yielded pure compound 1c (2.44 g, 28%) as a colorless oil.

$^1$H NMR (CDCl$_3$) d 7.76 (s, 1 H), 6.63 (s, 1 H), 6.47 (s, 1 H), 2.35 (m, 6 H), 1.29 (t, J=9.7 Hz, $^2$J ($^{119}$Sn—H)=56.8 Hz, 6 H); $^{119}$Sn NMR (CDCl$_3$) 100.7 ppm; IR (thin film) 1445, 1355, 1240, 1205, 1145, 1065, 745, 700 cm$^{-1}$; MS (m/z) 1228 (M$^+$), 1161 (M$^+$-furyl), 881 (M$^+$—CH$_2$CH$_2$C$_6$F$_{13}$).

11. Preparation of tris (3,3,4,4,5,5,6,6,7,7,8,8,8-Tridecafluorooctyl)(2'-pyridyl)tin, (tris (2-Perfluorohexylethyl) (2'-pyridyl)tin) (1d):

To the Grignard reagent prepared from 2-bromopyridine (822 mg, 5.20 mmol) and magnesium (146 mg, 6.20 mmol) in dry ether (30 mL) was added a solution of 2 (2.48 g, 2.00 mmol) in dry ether (5 mL). After refluxing for 1 min., the reaction was stirred for 17 hours at 25° C. The reaction mixture was quenched with NH$_4$Cl solution. After separation, diluted with ether, and the organic phase was washed with deionized water and then dried over anhydrous MgSO$_4$. The solvent was evaporated to dryness, and the resulting residue was partitioned between toluene and FC-72. The two phases were separated. The FC-72 phase was washed with toluene and concentrated to afford pure compound 1d (2.18 g, 88%) as a pale yellow oil.

$^1$H NMR (CDCl$_3$) d 8.71 (d, J=4.3 Hz, 1 H), 7.58 (t, J=7.7 Hz, 1 H), 7.36 (d, J=7.3 Hz, 1 H), 8.20 (m, 1 H), 2.29 (m, 6 H), 1.34 (t, J=8.2 Hz, $^2$J ($^{119}$Sn—H)=54.3 Hz, 6 H); $^{119}$Sn NMR (CDCl$_3$) 88.6 ppm; IR (thin film) 1570, 1450, 1360, 1240, 1205, 1145, 1060, 735, 700 cm$^{-1}$; MS (m/z) 1238 (M$^+$), 1161 (M$^+$-pyridyl), 892 (M$^+$—CH$_2$CH$_2$C$_6$F$_{13}$).

12. General Procedure for the Stille Couplings:

A sealed tube under nitrogen was charged with tin reactant (0.24 mmol), substrate (0.20 mmol), lithium chloride (25.4 mg, 0.60 mmol), dichlorobis(triphenylphosphine)palladium (II) (2.8 mg, 0.004 mmol), dry DMF (0.5 mL), and dry THF (0.5 mL) . The mixture was heated at 80° C. for 22 h. The solvent was evaporated and the residue was partitioned between water (10 mL), dichloromethane (15 mL), and FC-72 (10 mL). The three phases were separated and the dichloromethane phase was dried over anhydrous MgSO$_4$. Evaporation of the FC-72 phase provided chloro tris (3,3,4,4,5,5,6,6,7,7,8,8,8-tridecafluorooctyl)tin, (chloro tris (2-perfluorohexyl)ethyltin) 8, which was routinely recycled. Evaporation of the dichloromethane phase provided crude organic product, which was further purified by silica gel preparative TLC to provide the major cross-coupled product 6 (see yields in FIG. 4C) and a small amount (5–10%) of the symmetrical biaryl 7 derived from the tin reactant.

13. Chloro tris (3,3,4,4,5,5,6,6,7,7,8,8,8-Tridecafluorooctyl) Tin 8, (Chloro tris (2-Perfluorohexyl)ethyltin 8):

$^1$H NMR (CDCl$_3$) d 2.46 (m, 6 H), 1.53 (t, J=7.9 Hz, $^2$J ($^{119}$Sn—H)=47.6 Hz, 6 H); $^{119}$Sn NMR (CDCl$_3$) 273 ppm; IR (thin film) 1450, 1360, 1240, 1205, 1145, 1065, 735, 700 cm$^{-1}$; MS (m/z): 1161 (M$^+$—Cl), 849 (M$^+$—CH$_2$CH$_2$C$_6$F$_{13}$).

14. Representative Example of a Preparative Stille Coupling:

A sealed tube under nitrogen was charged with tin reactant 1a (2.97 g, 2.40 mmol), 1-bromo-4-nitrobenzene (404 mg, 2.00 mmol), lithium chloride (254 mg, 6.00 mmol), dichlorobis(triphenylphosphine)palladium(II) (28.1 mg, 0.04 mmol), dry DMF (5 mL), and dry THF (5 mL). The mixture was heated to 80° C. and a homogeneous solution resulted. The mixture was stirred at 80° C. for 22 h. After azeotropic evaporation with toluene at 75° C. (to remove THF and some of the DMF), the resulting residue was partitioned between water (40 mL), dichloromethane (60 mL), and FC-72 (40 mL). The three phases were separated. Evaporation of the FC-72 phase provided 2.31 g (80.6% from 1a) of tin chloride 8 as a colorless oil. The dichloromethane phase was washed three more times with water (40 mL) and FC-72 (40 mL). Evaporation of the combined FC-72 phases (including the first phase) provided 2.85 g (99.4% from 1a) of tin chloride 8. The final dichloromethane phase was dried over anhydrous MgSO$_4$ and evaporated to give yellow crystals free of fluorous reactant 1a and fluorous tin halides. The crude organic product was further purified by column chromatography on silica gel to provide the cross-coupled product, 4-nitrobiphenyl (337 mg, 85%) as yellow crystals, and the homo-coupled product, biphenyl (17 mg, 5%), as white crystals.

15. Representative Example of Recycle of Tin Reactants:

The tin chloride 8 (2.85 g) isolated by evaporation of FC-72 phase after the above Stille coupling was treated with a 3M solution of phenyl magnesium bromide in ether (1.04 mL, 3.12 mmol ) in dry ether (25 mL) under stirring at 25° C. for 6 h. The reaction mixture was hydrolyzed with $NH_4Cl$ solution and diluted with ether, and the organic phase was washed with deionized water then dried over anhydrous $MgSO_4$. The solvent was evaporated to dryness. Column chromatography on neutral alumina with hexane yielded pure compound 1a (2.85 g, 96% overall from 1a in the preceding section) as a colorless oil.

16. Bis |tris (3,3,4,4,5,5,6,6,7,7,8,8,8-Tridecafluorooctyl)tin Oxide, (Bis (tris (2-Perfluorohexyl)ethyltin|oxide |$(C_6F_{13}CH_2CH_2)_3Sn]_2O$; an Alternative Procedure for the Preparation of Tin Hydride 3:

Sodium hydroxide (254 mg, 6.33 mmol) in 8.4 mL of water was added to a solution of tris (2-perfluorohexyl) ethyltin bromide (5.23g, 4.22 mmol) in acetone (55 mL) . The mixture was heated at reflux for 12 h. The solvents mixture was evaporated. To the residue was added 10 ml of anhydrous toluene, and the resulting solution heated in a reflux apparatus equipped with a Dean-Stark type water trap for 12 h. The toluene solution was evaporated and the residue was dried over $P_2O_5$ in a vacuum desiccator for 12 h. The residue was extracted with dried hexane. The organic fraction collected was concentrated yielding the bis |tris (2-perfluorohexyl)ethyltin| oxide (3g, 61%) as a viscous yellow oil.

$^1H$ NMR ($CDCl_3$) d 2.45 (m, 12H); 1.55 (t, J=8.3 Hz, $^2J$ ($^{119}Sn$—H)=53.4 Hz, 12 H); $^{119}Sn$ NMR ($CDCl_3$) 165.54 ppm.

A mixture of bis |tris (2-perfluorohexyl)ethyltin| oxide (3 g, 1.28 mmol) and polymethylhydrosiloxane (191 mL; 3.22 mmol) was stirred at 25 ° C. for 12 h. After addition of ether, the presence of the tin hydride was shown by TLC comparison with an authentic sample.

17. Preparation of tris (3,3,4,4,5,5,6,6,7,7,8,8,8-Tridecafluorooctyl)allyltin, (tris (2-perfluorohexylethyl) allyltin), |$(C_6F_{13}CH_2CH_2)_3SnCH_2CHCH_2$|:

Allylmagnesium bromide (0.10 ml, 0.10 mmol) 1M in ether was added to a solution of 2 (100 mg, 0.08 mmol) in ether (4 mL). The mixture was heated at reflux for 2 h with stirring. To the reaction cooled to 0° C., and a saturated solution of aqueous ammonium chloride (3 ml) and ether (5 ml) were added. The two phases were separated and the aqueous phase was extracted twice with ether (2×10 ml). The ether phase was dried over $MgSO_4$ yielding, after evaporation, the allyl derivative (62 mg, 64%) as a white oil.

$^1H$ NMR ($CDCl_3$) d 5.95 (m, 1H); 5.0-4.8 (m, 2H); 2.30 (m, 6H); 1.95 (d, 2H, J=9 Hz); 1.20 (t, J=8.3 Hz, 6H).

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method for carrying out a chemical reaction, comprising the steps of:
    forming an organic/fluorous solubilizing liquid phase comprising a solvent system, the solvent system adapted to substantially solubilize a fluorous reaction component, the fluorous reaction component function-alized to comprise at least one fluorous moiety having the formula $(R)_d(Rf)_e$, wherein $(R)_d$ is an organic spacer group and may be present or absent and d is an integer equal to at least zero and $(Rf)_e$ is at least one fluorous group and e is a whole number, the solvent system also being selected to substantially solubilize at least one organic reaction component convertible in the presence of the fluorous reaction component to a product;
    contacting the fluorous reaction component and the organic reaction component in the organic/fluorous solubilizing liquid phase under conditions suitable to produce the product; and
    after production of the product, causing a phase separation into a fluorous liquid phase and an organic phase, the fluorous reaction component comprising a sufficient number of fluorous moieties to render any excess of the fluorous reaction component and any fluorous byproduct of the fluorous reaction component preferentially partitionable into the fluorous phase.

2. The method of claim 1 further comprising the step of separating the product from the fluorous reaction component.

3. The method of claim 1 wherein the reagent is a catalyst.

4. The method of claim 1 wherein the fluorous reaction component has the formula $XM((R)_d(Rf)_e)_3$, wherein M is selected from the group consisting of tin, germanium and silicon, and X is a moiety selected to react with the organic reaction component.

5. The method of claim 4 wherein the fluorous reaction component has the formula $$XM|(R)(Rf)|_3,$$

wherein X is H, F, Cl, Br, I, $N_3$, $OR^1$, OH, OOH, $OOR^1$ $SR^1$, $SeR^1$, CN, NC, $NR^1R^2$, a cyclic group, a heterocyclic group, a linear or branched alkyl group of 1 to 20 carbons, an alkenyl group, an alkynyl group, an acyl group, M'((R') (Rf))$_3$, OM'((R') (Rf))$_3$ or OOM'((R')Rf))$_3$, wherein M' is Si, Ge, and Sn, and wherein $R^1$ and $R^2$ are each independently the same or different H, a linear or branched alkyl group, a cyclic alkyl group, an alkylsulfonyloxy group, a perfluoroalkylsulfonyloxy group, an acyl group, or a perfluoroacyloxy group, and wherein M is Ge or Sn, and wherein R and R' are each independently the same or different an alkylene group of 1 to 6 carbons and wherein Rf and Rf are each independently a linear perfluoroalkyl group of 3 to 20 carbons, a branched perfluoroalkyl group of 3 to 20 carbons, and a hydrofluoroalkyl group of 3 to 20 carbons, the hydrofluoroalkyl group comprising up to one hydrogen atom for each two fluorine atoms.

6. The method of claim 5 wherein X is an aryl group, or a heteroaryl group.

7. The method of claim 5 wherein M is Sn.

8. The method of claim 7 wherein X is H, F, Cl, Br, $N_3$, OH, $OSn(CH_2CH_2Rf)_3$, an allyl group, a phenyl group, a 4-methoxyphenyl group, a 2-pyridyl group or a 2-furyl group.

9. The method of claim 7 wherein R is a linear alkylene group of 1 to 6 carbons.

10. The method of claim 9 wherein R is —$CH_2CH_2$—.

11. The method of claim 9 wherein Rf is a linear perfluoroalkyl chain of 6 to 12 carbons.

12. A chemical compound of the formula $$XM|(R)(Rf)|_3,$$

wherein X is H, F, Cl, Br, $N_3$, $OR^1$, OH, OOH, $OOR^1$ $SR^1$, $SeR^1$, CN, NC, $NR^1R^2$, a cyclic group, a heterocyclic group, an alkenyl group, an alkynyl group, an acyl group, M'((R')(Rf'))$_3$, OM'((R')(Rf'))$_3$ or OOM'((R')Rf'))$_3$, wherein M' is Si, Ge, and Sn, and wherein R$^1$ and R$^2$ are each independently the same or different H, a linear or branched alkyl group, a cyclic alkyl group, an alkylsulfonyloxy group, a perfluoroalkylsulfonyloxy group, an acyl group, or a perfluoroacyloxy group, and wherein M is Ge or Sn, and wherein R and R' are each independently the same or different an alkylene group of 1 to 6 carbons and wherein Rf and Rf' are each independently a linear perfluoroalkyl group of 3 to 20 carbons, a branched perfluoroalkyl group of 3 to 20 carbons, and a hydrofluoroalkyl group of 3 to 20 carbons, the hydrofluoroalkyl group comprising up to one hydrogen atom for each two fluorine atoms.

13. The chemical compound of claim 12 wherein X is an aryl group, or a heteroaryl group.

14. The chemical compound of claim 12 wherein M is Sn.

15. The chemical compound of claim 14 wherein X is H, F, Cl, Br, N$_3$, OH, OSn(CH$_2$CH$_2$Rf)$_3$, an allyl group, a phenyl group, a 4-methoxyphenyl group, a 2-pyridyl group or a 2-furyl group.

16. The chemical compound of claim 14 wherein R is a linear alkylene group of 1 to 6 carbons.

17. The chemical compound of claim 16 wherein R is —CH$_2$CH$_2$—.

18. The chemical compound of claim 14 wherein Rf is a linear perfluoroalkyl chain of 6 to 12 carbons.

* * * * *

UNITED STATES PATENT AND TRADEMARK OFFICE
CERTIFICATE OF CORRECTION

| | |
|---|---|
| PATENT NO. | : 5,777,121 |
| APPLICATION NO. | : 08/671945 |
| DATED | : July 7, 1998 |
| INVENTOR(S) | : Dennis P. Curran et al. |

It is certified that error appears in the above-identified patent and that said Letters Patent is hereby corrected as shown below:

Column 1, line 1, inset the following paragraph.

-- Governmental Interests
 This invention was made with government support under grant #R01 GM033372 awarded by the National Institutes of Health and under grant #CHE-9501345 awarded by the National Science Foundation. The government has certain rights in this invention. --

Signed and Sealed this

Thirtieth Day of January, 2007

JON W. DUDAS
*Director of the United States Patent and Trademark Office*